United States Patent
Tanaka

[11] Patent Number: 5,368,831
[45] Date of Patent: Nov. 29, 1994

[54] CERAMIC INLAY AND PROCESS FOR MAKING SAME

[75] Inventor: Asami Tanaka, Skokie, Ill.

[73] Assignee: Asami Tanaka Dental Enterprises Inc., Skokie, Ill.

[21] Appl. No.: 821,489

[22] Filed: Jan. 15, 1992

[51] Int. Cl.⁵ ............................................. A61C 5/04
[52] U.S. Cl. .................................................. 433/226
[58] Field of Search ............... 433/226, 227, 228.1, 433/218, 207; 264/19

[56] References Cited

U.S. PATENT DOCUMENTS

| | | | |
|---|---|---|---|
| 3,997,637 | 12/1976 | Rogers | 264/19 |
| 4,392,829 | 7/1983 | Tanaka | 433/222.1 |
| 4,431,451 | 2/1984 | Wabie et al. | 433/199.1 X |
| 4,579,530 | 4/1986 | McLaughlin | 433/213 X |
| 4,794,774 | 1/1989 | Clark et al. | 264/19 X |
| 4,929,420 | 5/1990 | Cook | 433/207 X |
| 4,940,637 | 7/1990 | Skoker et al. | 433/218 X |
| 4,980,124 | 12/1990 | Dinner | 433/227 X |
| 4,997,723 | 3/1991 | Tanaka | 433/207 X |
| 5,104,323 | 4/1992 | Mertens | 433/226 |
| 5,106,303 | 4/1992 | Oden et al. | 433/218 X |
| 5,186,626 | 5/1991 | Tanaka | 433/208 X |

*Primary Examiner*—Gene Mancene
*Assistant Examiner*—Nicholas D. Lucchesi
*Attorney, Agent, or Firm*—Roper & Quigg

[57] ABSTRACT

A process for making a ceramic inlay for filling a cavity in a tooth. A piece of metal foil is pressed into a depression in a jig, where the depression approximates the shape of the cavity; the pressed metal foil is annealed and the pressing and annealing steps are repeated until the foil has a concave depression roughly the same size and shape as the cavity. A ceramic layer is built up on the concave foil to form a ceramic inlay substantially reconstructing the tooth.

13 Claims, 2 Drawing Sheets

CERAMIC INLAY AND PROCESS FOR MAKING SAME

TECHNICAL FIELD

This invention relates to an improved ceramic inlay for filling cavities in teeth. More specifically, this invention relates to an improved ceramic inlay for filling cavities in teeth comprising a layer of translucent ceramic material bonded to a foil layer.

BACKGROUND ART

Inlays for filling cavities in teeth are frequently made of metal, such as silver. These inlays have relatively long lifetimes, but they are not aesthetically pleasing, being visible in the mouth as a gray area. Patients with pure metal inlays are frequently self-conscious when smiling or yawning. Because natural dentin is translucent and allows a significant amount of visible light to pass through it, metal inlays in the center of even large teeth, such as molars, can be visible as a grayish, dead-looking spot in the patient's mouth.

One alternative to such solid metal inlays is the use of inlays made of plastic. While such plastic inlays are easy to work with and present acceptable aesthetic characteristics, such inlays have inferior wear characteristics. Plastic inlays wear extremely quickly, especially in occlusal inlays.

Another alternative is an inlay made of translucent ceramic material. These ceramic inlays are also aesthetically pleasing because ceramic is similar to the natural tooth structure. Thus, such inlays alleviate much of the patient's mental discomfort regarding mouth appearance. However, these ceramic inlays also have inferior strength characteristics. Because such inlays lack support, they tend to fracture after a few years of normal occlusions with opposing teeth. Moreover, inlays made of ceramic tend to fracture at the margin (the edge of the inlay adjacent the remainder of the natural tooth). In such cases, it is likely that organic matter will become lodged between the fractured inlay and the remainder of the natural tooth, leading to further tooth decay.

DISCLOSURE OF INVENTION

The present invention provides an improved ceramic inlay. The ceramic inlay is made with a thin layer of foil bonded to the ceramic. This metal foil layer can remain as part of the inlay and can be removed, in whole or in part. The ceramic inlay is stronger than plastic inlays, stronger than previous ceramic inlays, and has better aesthetic properties than metal inlays. The layer of foil increases the strength of the inlay to a greater degree than expected for combining metal and ceramic. The inlay has a longer lifetime than ceramic inlays and even has a longer lifetime than metal inlays made of soft metals. The inlay looks more like a natural tooth than a metal inlay, because it is made primarily of ceramic, which the dentist can form into the shape of a natural tooth, and which is the same color as a natural tooth.

In one embodiment of this invention, the foil layer can be so thin that it is invisible to the naked eye, further enhancing the aesthetic properties of this invention. This embodiment is facilitated by the use of an alloy of platinum, indium and gold disclosed in U.S. Pat. No. 4,997,723 issued Mar. 5, 1991, the complete disclosure of which is incorporated herein by reference.

In another embodiment of this invention, the ceramic inlay has a thin strip of the foil layer removed in order to improve the passage of light through the tooth containing the inlay. In such a tooth, the translucence of the tooth containing the inlay is more similar to that of a natural tooth, thus further enhancing the aesthetic properties of this invention.

The invention further provides a process for making the improved ceramic inlay that is suitable for filling cavities of any size or shape. An annealing step allows for making depressions in foil of any desired depth without tearing the foil or causing it to wrinkle. The annealing step, performed after a pressing step, strengthens the metal and permits a further pressing step. After pressing and annealing the foil into roughly its desired shape, the foil can be formed to the shape of the cavity using an isotactic press, and no wrinkles or folds in the foil will result.

The invention further provides a jig for making depressions in the foil of the desired size and shape. The jig has several rows of depressions, each row containing depressions of the same shape, but where each depression in the row is deeper than the preceding depression. Various shapes of depression are provided: plus or cross-shaped depressions, square-shaped depressions, and round depressions.

MODES FOR CARRYING OUT THE INVENTION

The embodiments disclosed herein are the preferred embodiments of this invention and should not be construed as limiting the invention in any way.

Inlays for filling cavities in teeth may be made of a variety of materials, but usually metal or ceramic is used. Traditionally, an inlay is made of one material. Other inlays are made when a hollow metal structure is cast and then the hollow of the structure is filled with ceramic material. However, inlays which have a substantial metal portion suffer from the aesthetic disadvantages of metal inlays, the strength disadvantages of ceramics and a long processing time, because casting is a relatively time-consuming method of metal preparation.

The inlays of the present invention comprise a metal foil and ceramic, providing a strong inlay that also satisfies the aesthetic goals of dental restorations.

Figure 1:
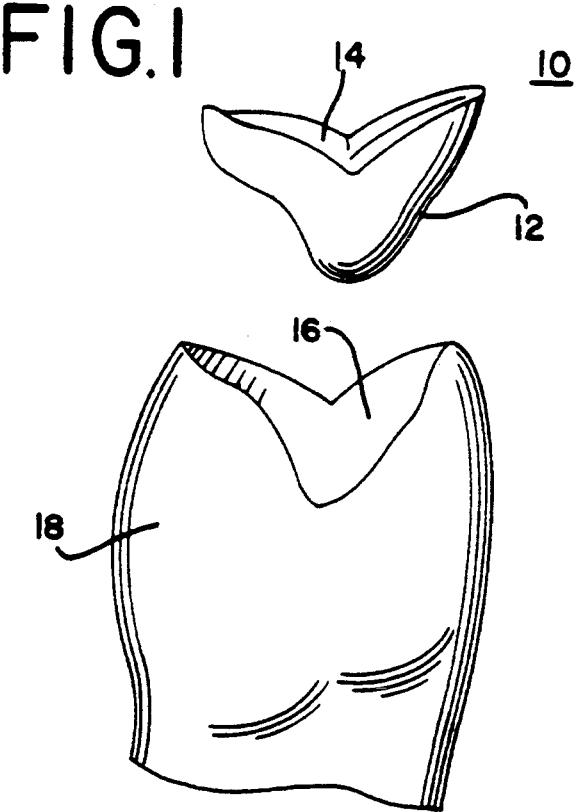
FIG. 1 is a schematic side-view of the ceramic inlay of this investigation.

Referring to FIG. 1, the ceramic inlay 10 of the present invention comprises a ceramic layer 14 that is the same shape as cavity 16 in a tooth 18, and is slightly smaller than the cavity 16. The slight (10–50 micron) decrease in size is to allow the foil layer 12 to fit between the walls of the cavity 16 and the ceramic layer 14. This foil layer is uniformly fitted to the ceramic layer 14, and bonded thereto using normal dental adhesive. The completed ceramic inlay 10, with ceramic layer 14 and foil layer 12 fits very snugly into the cavity 16. For added security, the inlay 10 can be affixed to the tooth 18 with normal dental adhesive.

The ceramic layer 14 can be any ceramic or porcelain used for dental applications, and is preferably non-translucent dentin powder, which is off-white in its raw state, but becomes a translucent white color after baking at 900°–950° C. The translucence of this ceramic provides a dental restoration that has light transmission properties similar to those of natural teeth. Thus, these restorations when bonded into the patient's mouth have an appearance more like a natural tooth than prior art restorations.

The foil layer 12 can be any foil used in other dental applications such as crowns and bridges. Preferably the foil layer is made of a three-component alloy disclosed in U.S. Pat. No. 4,997,723. A foil made of this alloy has a superior appearance. Furthermore, this alloy can be stretched to a thickness of less than 10 microns. Since the naked human eye can obviously detect only those objects with a thickness of 20 microns or greater, the foil layer 12 can be stretched to a thickness that is functionally invisible. Then the ceramic inlay of this invention is implanted in the cavity 16, the foil layer 12 is continuous with the walls of the cavity 16. Thus, the foil layer is only visible as a line between the ceramic layer 14 and the natural tooth 18.

A metal foil less than 10 microns in thickness in no way diminishes the contribution to the strength of the inlay provided by the foil.

Figure 2:
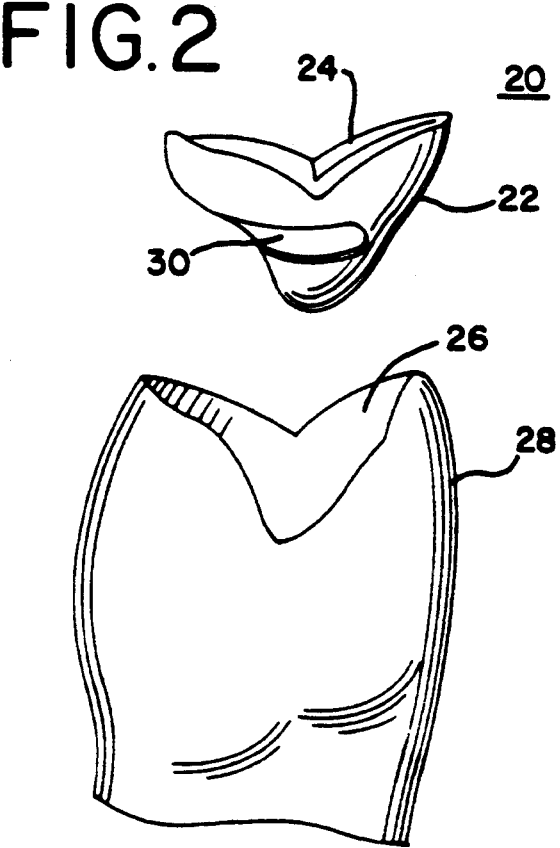
FIG. 2 is a schematic side-view of an embodiment of the ceramic inlay of this invention having a thin strip of the foil removed.

Referring to FIG. 2, in another embodiment of the ceramic inlay 20 of this invention, a strip 30 of ceramic 24 may be exposed by removing a small strip of the foil layer 22. The removal of the foil layer can be accomplished by grinding, or, in most cases by simply peeling the foil layer off, much like adhesive tape can be peeled from a surface. When this modified ceramic inlay 20 is implanted in the cavity 26 in tooth 28, the strip of exposed ceramic 30 is in close proximity to or is substantially contacting the walls of the cavity 26, separated only by the dental adhesive used to bond the inlay 20 in place. Light that passes through the tooth may thus also pass partially through the ceramic inlay 20 via the strip of exposed ceramic 30. The light transmission properties of a tooth containing this kind of inlay are more similar to the light transmission properties of teeth containing inlays of solid metal. The light transmission properties are also enhanced by exposing regions of shapes other than strips, or exposing more than one region.

The process of making the ceramic inlay of this invention begins with the dentist making a mold or die of the patient's mouth. The die is make by putting a soft plastic material that is capable of becoming hard into the cavity and allowing or causing it to harden. The plastic may be any material capable of retaining the shape of the cavity after it hardens. In addition to plastic, other materials may be used. Metals, epoxies and stone, such as gypsum, are all suitable.

Figure 4:
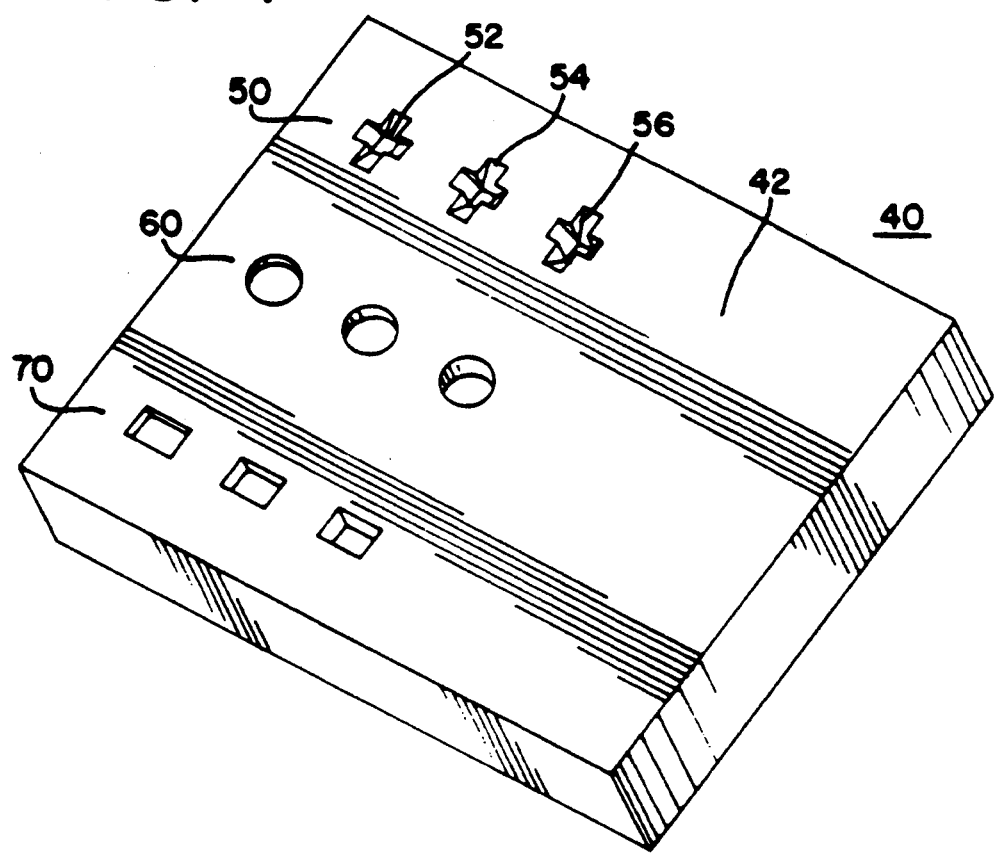
FIG. 4 is a schematic of the jig of this invention.

Before, after, or while the above die is made, the metal foil is formed into the rough shape of the die. This is accomplished using a jig, as shown in FIG. 4. The jig 40 contains a flat surface 42 and rows of depressions. FIG. 4 shows three rows 50, 60 and 70; however, jigs with more or fewer rows of depressions are equally suitable. Each row of depressions contains one or more depressions of similar shape but varying depths. For example, row 50 of plus-shaped depressions contains three depressions 52, 54, and 56, wherein the first depression 52 is not as deep as the third depression 56. Three depths of depressions are not critical for this invention, and more or fewer depressions will work just as effectively.

The jig contains depressions for each of the typical shapes of cavities. Thus, in the preferred embodiment, the depressions in the first row 50 are plus-shaped, those in the second row 60 are round, and those in the last row 70 are rectangular. The invention is not limited to depressions of these shapes, and those skilled in the art will know other shapes which are additionally desirable. Further, a specific jig could be created for a specific inlay.

In the process of this invention the jig is used to facilitate foil stretching. The foil, obtained initially in a flat state, is placed over the shallowest depression of the shape roughly corresponding to the shape of the cavity to be filled. The foil is then pressed gently into the depression. It is preferred to use a rubber-tipped utensil for pressing the foil. When the foil has been completely pressed into the depression, it is annealed by heating it to 900°–950° C. The annealing step relives the internal stress in the metal. If the foil is roughly the same shape as the die, then the foil is ready to be closely fitted to the die using isostatic pressure, as described below; otherwise, pressing the foil on the jig is resumed.

After the annealing step, pressing the foil is resumed, if necessary, using the second depression, which is deeper than the first depression but is of the same shape or by using a different shape. When the foil is pressed into this depression, it is again annealed. If the foil is still not roughly the same shape as the die, pressing and annealing may be done on the third depression, or on any successive depressions as may be necessary to form the foil into the rough shape.

After forming the foil into roughly the shape of the cavity, the die is covered with the foil and the foil and die are subjected to isostatic pressure as described in U.S. Pat. No. 4,794,774. Then, the foil is removed from the die, and the ceramic is bonded to the foil. The ceramic layer is built up using standard techniques, including baking at 900°–960° C. (or other temperatures appropriate for the ceramic material). The mold is not used any further, thus the mold does not need to be made of a material able to withstand the firing process.

Thus, the present invention provides of method of making an inlay which is simpler and quicker than traditional methods. In the present invention, the original mold of the cavity is used to form the foil layer. Traditionally, the original mold would be used to cost a refractory mold which, in turn, would be used in making the inlay. By eliminating the use of the refractory mold, the process is simplified and the resulting inlay fits more accurately to the cavity because it is well recognized that each step results in some loss of detail and accuracy. Thus the present invention has several advantages over traditional methods.

The alternative embodiment of the ceramic inlay that has improved light transmission properties is made by the above-described process, followed by removing a region of foil. The removal step may be accomplished using any recognized grinding method or by peeling the foil.

Figure 3:
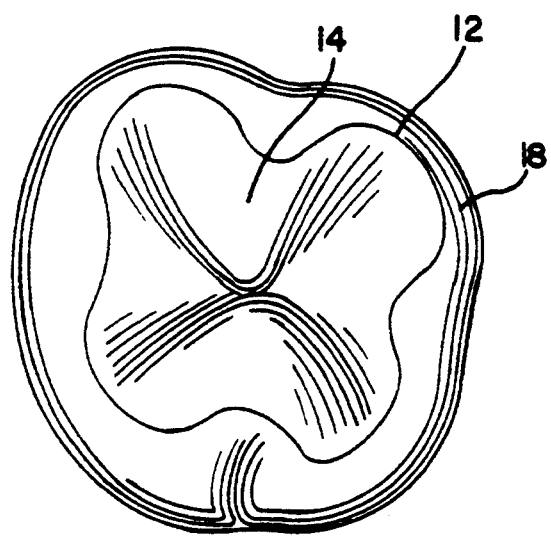
FIG. 3 is a top-view schematic of the ceramic inlay.

Finally, the finished inlay is affixed to the tooth in the normal fashion. FIG. 3 shows a reconstructed tooth using the invention. The numerals are the same as for FIG. 1.

Having described the invention, what is claimed is:

1. A ceramic inlay for filling a cavity in a tooth, comprising:

a baked ceramic layer having an upper portion and a lower portion, said upper portion being a reconstruction of the outer surface of the tooth; and a layer of a thin metal foil bonded to at least a region of said lower portion of said baked ceramic layer said layer of thin metal foil closely fitting the walls of the cavity in the tooth.

2. The ceramic inlay of claim 1, wherein the thickness of the foil layer is less than about 20 microns.

3. The ceramic inlay of claim 1, wherein the thickness of the foil layer is less than about 10 microns.

4. The ceramic inlay of claim 1, wherein said layer of thin metal foil is bonded to and covers substantially the entirety of said lower portion of said baked ceramic layer so that no substantial region of said lower portion of said baked ceramic layer is exposed to the walls of cavity in the tooth.

5. A process for making a ceramic inlay for filling a cavity in a tooth, comprising the steps of:

pressing a piece of metal foil into a depression in a jig, said depression approximate in shape to said cavity;

annealing said pressed metal foil;

repeating said pressing and annealing steps until said foil has a concave depression roughly the same size and shape as the cavity; and building up a ceramic layer on said concave foil to form a ceramic inlay substantially reconstructing the tooth.

6. The process of claim 5, wherein said annealing is accomplished by heating.

7. The process of claim 5, further comprising the step of:

removing a strip of foil from said ceramic inlay.

8. The process of claim 5 wherein said jig comprises a flat surface having a plurality of depressions, each of said depressions having substantially the same shape, and each of said depressions having a different depth.

9. A process for-making a ceramic inlay for filling a cavity in a tooth, comprising the steps of:

making a die of the cavity;

pressing a piece of foil into a depression in a jig, said depression approximate in shape to said cavity;

annealing said pressed metal foil;

repeating said pressing and annealing steps until said foil has a concave depression roughly the same size and shape as the cavity;

covering said die with said foil;

subjecting said foil covered die to isostatic pressure to uniformly press said foil onto said die;

removing said uniformly pressed foil from said die; and building up a ceramic layer on said concave foil to form a ceramic inlay substantially reconstructing the tooth.

10. The process of claim 9, wherein said annealing is accomplished by heating.

11. The process of claim 9, further comprising the step of removing a strip of foil from said ceramic inlay after said step of building up said ceramic layer.

12. A ceramic inlay for filling a cavity in a tooth comprising:

a baked ceramic layer having an upper portion and a lower portion, said upper portion being a reconstruction of the outer surface of the tooth; and a layer of a thin metal foil bonded to at least a region of said lower portion of said baked ceramic layer said layer of thin metal foil closely fitting the walls of the cavity in the tooth wherein said layer of thin metal foil is bonded to only a region of and does not cover the entirety of said lower portion of said baked ceramic layer resulting in at least one region of said lower portion of said baked ceramic layer being exposed to the walls of the cavity in the tooth.

13. The ceramic inlay of claim 12, wherein said baked ceramic layer comprises a substantially translucent material.

* * * * *